(12) United States Patent
Guillemoles et al.

(10) Patent No.: US 9,297,764 B2
(45) Date of Patent: Mar. 29, 2016

(54) METHOD FOR DETERMINING CHARACTERISTICS OF A PHOTOCONVERTER WITHOUT CONTACT

(75) Inventors: Jean-François Guillemoles, Paris (FR); Arnaud Etcheberry, Colombes (FR); Isabelle Gerard, Gif sur Yvette (FR); Pierre Tran-Van, Courbevoie (FR)

(73) Assignees: CENTRE NATIONAL DE LA RECHERCHE SCIENTIFIQUE—CNRS—, Paris (FR); ELECTRICITE DE FRANCE, Paris (FR); UNIVERSITE DE VERSAILLES SAINT-QUENTIN-EN-YVELINES, Versailles (FR)

( * ) Notice: Subject to any disclaimer, the term of this patent is extended or adjusted under 35 U.S.C. 154(b) by 786 days.

(21) Appl. No.: 13/574,975

(22) PCT Filed: Feb. 7, 2011

(86) PCT No.: PCT/FR2011/050242
§ 371 (c)(1),
(2), (4) Date: Nov. 28, 2012

(87) PCT Pub. No.: WO2011/095752
PCT Pub. Date: Aug. 11, 2011

(65) Prior Publication Data
US 2013/0066574 A1 Mar. 14, 2013

(30) Foreign Application Priority Data
Feb. 5, 2010 (FR) ...................................... 10 50845

(51) Int. Cl.
*G01R 31/00* (2006.01)
*G06F 19/00* (2011.01)
(Continued)

(52) U.S. Cl.
CPC ........ *G01N 21/6489* (2013.01); *G01N 21/4738* (2013.01); *H02S 50/10* (2014.12); *G01N 2021/6493* (2013.01); *G01N 2201/065* (2013.01)

(58) Field of Classification Search
CPC ............ C01N 21/4738; G01N 21/6489; G01N 2201/065; G01N 2021/6493; H02S 50/10; H01G 9/2004; H01G 9/2031; H01G 9/2013; H01M 14/005; H01M 2300/0025; H01M 2300/0022; Y02E 60/13; Y02E 10/542
USPC .................. 702/64; 136/263; 252/500, 62, 2; 257/443, E31.001; 429/188, 339, 340
See application file for complete search history.

(56) References Cited

U.S. PATENT DOCUMENTS

| | | | | |
|---|---|---|---|---|
| 6,297,443 B1* | 10/2001 | Nakajima et al. | ............. | 136/258 |
| 8,227,733 B2* | 7/2012 | Higuchi et al. | ............... | 250/206 |

(Continued)

FOREIGN PATENT DOCUMENTS

| | | | |
|---|---|---|---|
| JP | 09292281 A | * | 11/1997 |
| JP | H09292281 A | | 11/1997 |
| JP | 2003215041 A | * | 7/2003 |

OTHER PUBLICATIONS

French Search Report from corresponding French Patent Application No. FR 1050845 Report Dated Apr. 13, 2011.
(Continued)

*Primary Examiner* — Carol S Tsai
(74) *Attorney, Agent, or Firm* — Miller, Matthias & Hull LLP

(57) ABSTRACT

The invention relates to a method for determining the maximum open circuit voltage and the power that can be output by a photoconverter material subject to a measurement light intensity, the method including the following steps: measuring the photoluminescent intensity of the material, measuring the absorption rate of the photoconverter material at a second wavelength substantially equal to the photoluminescent wavelength of the photoconverter material, determining the maximum open circuit voltage of the photoconverter material with the measurement light intensity by means of the absorption rate and the photoluminescent intensity measured at substantially the same wavelength; said invention being characterized in that the light source and the photoconverter material are arranged such that the angular distributions of the rays incident on and emitted by the lit surface of the material and collected by the detector are substantially identical.

8 Claims, 1 Drawing Sheet

(51) Int. Cl.
*G01N 21/64* (2006.01)
*G01N 21/47* (2006.01)
*H02S 50/10* (2014.01)

(56) References Cited

U.S. PATENT DOCUMENTS

| | | | |
|---|---|---|---|
| 8,257,615 B2* | 9/2012 | Matsui et al. | 252/500 |
| 8,415,559 B2* | 4/2013 | Basol | 136/265 |
| 8,933,327 B2* | 1/2015 | Sasaki et al. | 136/261 |
| 2005/0099623 A1 | 5/2005 | Takeuchi et al. | |
| 2009/0032105 A1* | 2/2009 | Inoue et al. | 136/263 |
| 2009/0217979 A1* | 9/2009 | Yoneya et al. | 136/258 |
| 2010/0243863 A1* | 9/2010 | Higuchi et al. | 250/206 |
| 2011/0129714 A1* | 6/2011 | Kelzenberg et al. | 429/111 |
| 2011/0146756 A1* | 6/2011 | Sasaki et al. | 136/246 |

OTHER PUBLICATIONS

International Search report from corresponding PCT Application No. PCT/FR2011/050242 Report Dated Apr. 13, 2011.

Bauer, G.H., "Quasi-Fermi Level Splitting and Identification of Recombination Losses from Room Temperature Luminescence in $Cu(In_{1-x},Ga_x)Se_2$ Thin Films Versus Optical Band Gap", The Solid Films, Jun. 1, 2005, pp. 410-414, vol. 480-481, Elsevier.

Smestad, Greg P., "Absorptivity as a Predictor of the Photoluminescence Spectra of Silicon Solar Cells and Photosynthesis", Solar Energy Materials and Solar Cells, Aug. 1, 1995, pp. 57-71, vol. 38, No. 1/4, Elsevier, Amsterdam.

Bauer, G. H. et al., "Open Circuit VOltage from Quasi-Fermi Level Splitting in Polycrystalline $Cu(In, Ga)Se_2$ Films by Photoluminescence with Lateral Sub-Micron Resolution", Conference record of the IEEE photovoltaic specialists conference, May 19, 2002, pp. 700-703, vol. Conf. 29, IEEE.

Schubert, Martin C., "Spatially Resolved Lifetime Imaging of Silicon Wafers by Measurement of Infrared Emission", Journal of Applied Physics, 2003, pp. 4139-4143, vol. 94, No. 6, American Institute of Physics.

Trupke, T. et al., "Suns-Photoluminescerte: Contactless Determination of Current-Voltage Characteristics of Silicon Wafers", Applied Physics Letters, 2005, pp. 093503-1-093503-3, vol. 87, No. 9, American Institute of Physics.

Trupke, T. et al., "Photoluminescence Imaging of Silicon Wafers", Applied Physics Letters, 2006, pp. 044107-1-044107-3, vol. 89, No. 4, American Institute of Physics.

Rau, U. "Reciprocity Relation Between Photovoltaic Quantum Efficiency and Electroluminescent Emission of Solar Cells", Physical Review, Aug. 2, 2007, pp. 085303-1-085303-8, vol. 76, The American Physical Society.

Wurfel, P., "The Chemical Potential of Radiation", J. Phys. C: Solid State Phys., Jan. 18, 1982, pp. 3967-3985, vol. 15, The Institute of Physics, Karlsruhe, West Germany.

Smestad, G. et al. "Luminescence and Current-Voltage Characteristics of Solar Cells and Optoelectronic Devices", Solar Energy Materials and Solar Cells, Oct. 23, 1991, pp. 51-71, vol. 25, Elsevier Science Publishers B.V., North-Holland.

Decision of Rejected Application No. JP 2012-551670 reported on Jul. 6, 2015.

G. H. Baue, et al., "Quasi-Fermi level splitting an identification of recombination losss from room temperature luminescence in $Cu(In_{1-x} Ga_x)Se_2$ thin films versus optical band gap", Thin Solid Films, 480-481 (2005) 410-414.

\* cited by examiner

METHOD FOR DETERMINING CHARACTERISTICS OF A PHOTOCONVERTER WITHOUT CONTACT

CROSS-REFERENCE TO RELATED APPLICATIONS

This application is a 35 USC §371 U.S. national stage filing of International Patent Application No. PCT/FR2011/050242 filed on Feb. 7, 2011, which claims priority under the Paris Convention and 35 USC §119 to French Patent Application No. 10 50845, filed on Feb. 5, 2010.

FIELD OF THE DISCLOSURE

The invention relates to a method for determining the maximum open circuit voltage of a photoconverter material.

BACKGROUND OF THE DISCLOSURE

Solar cells, for example thin film cells such as cells of amorphous silicon, CdTe, GaAs, or other III-V compounds, or cells based on semiconductor compounds such as copper, gallium, and indium diselenide, are based on a stack of layers of photoconverter materials and current collection materials.

Given the difficulty of developing the complete device, it is preferable to take care in choosing the photoconverter material.

To make the best choice of photoconverter material, one determines the optoelectronic properties of the material in order to deduce the efficiency it would be possible to obtain with the complete device.

For this purpose, particularly for thin film technology, it is often necessary to develop specific technological steps to eliminate the influence of contacts which otherwise could influence or even dictate the properties of the contacts/photoconverter material system. Optimization of providing these contacts can therefore be time-consuming without contributing any true added value to the final photovoltaic device, in which laying out contacts is of course necessary but is subject to other technological constraints.

A need therefore exists for a method for directly measuring on the photoconverter material the optoelectronic properties which allow evaluating the efficiency of a solar cell obtained using this photoconverter material, with no need to shape or process the material or laying out the contacts.

SUMMARY OF THE DISCLOSURE

The invention proposes meeting this need by providing a method for determining, without contact, the maximum open circuit voltage of a photoconverter material.

The invention proposes a method for determining the maximum open circuit voltage (Vco) of a photoconverter material exposed to a measurement light intensity I0, said method comprising the following steps:
the photoluminescence intensity of the photoconverter material is measured by illuminating the photoconverter material using a first light source at a first light intensity I1 and at a first wavelength ($\lambda$1) corresponding to a first excitation energy greater than the absorption energy (Eg) of the photoconverter material, the first light intensity (I1) being substantially equal to the measurement light intensity I0,
the absorptivity of the photoconverter material is measured at a second wavelength ($\lambda$2) substantially equal to the photoluminescence wavelength of the photoconverter material, by illuminating the photoconverter material using a second light source at the second wavelength ($\lambda$2) and at a second light intensity I2, and
the maximum open circuit voltage (Vco) of the photoconverter material at the measurement light intensity I0 is determined using the absorptivity and the photoluminescence intensity, both measured at substantially the same wavelength,
wherein the light source and the photoconverter material are arranged such that the angular distributions of the rays incident on and emitted by the illuminated surface of the material and collected by the detector are substantially the same.

Advantageously, the method of the invention allows directly determining the open circuit voltage achievable by a given photoconverter material, with no need to shape or process the material or laying out the contacts.

A method according to the invention may additionally comprise one or more of the following optional characteristics, individually or in any possible combination:
the open circuit voltage (Vco) is determined using the following equation:

$$I_{PL} = a(v2)\frac{2n_{v2}^2}{c^2}\frac{v^2}{\exp\left(\frac{hv-qVco}{kT}\right)-1},$$

where
$I_{PL}$ is the photoluminescence intensity of the photoconverter material, measured by illuminating the photoconverter material at the first light intensity I1, and in particular concerns the radiant energy density per frequency interval,
a(v2) is the absorptivity of the photoconverter, measured at the second wavelength ($\lambda$2=c*v2) substantially equal to the photoluminescence wavelength of the photoconverter material and at the second light intensity I2,
$n_{v2}$ is the optical index for the photoconverter material at the photoluminescence wavelength of the photoconverter material,
c is the speed of the electromagnetic radiation in a vacuum,
v is the frequency corresponding to the photoluminescence wavelength of the photoconverter material,
h is the Planck constant,
k is the Boltzmann constant,
T is the surface temperature of the photoconverter,
q is the value of an elementary charge, and
Vco is the open circuit voltage of the photoconverter material;
the photoconverter material, the first and second light sources, and the optical measurement device are arranged such that the solid angle of illumination of the photoconverter material is substantially equal to the solid angle of collection of the optical measurement device;
the photoconverter is placed in an integrating sphere structure such that it is indirectly illuminated by the first and second light sources; and
the measurements of photoluminescence intensity and/or absorptivity are made using a diode or spectrometer, possibly modulating the sample signal to increase sensitivity.

The invention also relates to a method for determining the energy efficiency of a photoconverter material, said method comprising the following steps:
the maximum open circuit voltage (Vco) of the photoconverter material is determined at a measurement light intensity I0 by a method of the invention, the photocurrent of the photoconverter material is determined by measuring the absorptivity of the material at a third light intensity I3 substantially equal to the measurement light intensity I0 and at different wavelengths, the energy efficiency of the photoconverter material is determined at the light intensity I0 according to:

Efficiency=*Vco*\**Icc*\**FF*/*Pinc*, where
Icc is the photocurrent of the photoconverter material,
Vco is the maximum open circuit voltage of the photoconverter material;
FF is the form factor of the photoconverter material, and
Pinc is the incident power.

The form factor FF can be calculated from one of the known formulas, for example the following formula:

FF=(vco−ln(0,7+vco))/(1+vco), with vco=Vco/k\*T.

The invention also relates to a method for determining the power extractible from a photoconverter material illuminated by a light source of intensity I0, said method comprising the following steps:

the maximum open circuit voltage Vco of the photoconverter material is determined, at a plurality of light intensities Ij of between I0/20 and I0, by a method of the invention, the photocurrent Icc of the photoconverter material is determined by a method of the invention, the power extractible from the photoconverter material is determined by plotting Icc\*Ij/I0 as a function of Vco(Ij).

The extractible power is obtained by plotting Icc\*Ij/I0 as a function of Vco(I0) and considering the surface area of the largest rectangle that can be drawn between the vertical axis passing through V=0
the horizontal line of ordinate I=I0
the above curve Icc\*Ij/I0 as a function of Vco(Ij)

The power value sought is equal to the surface area of the rectangle.

In one embodiment of the invention, the photocurrent of the photoconverter material is determined using the following equation:

Icc=∫a(v)Φ(v)dv, where
Icc is the determined photocurrent of the photoconverter material,
a(v) is the absorptivity of the photoconverter material at the measurement light intensity I0, and
Φ(v) is the incident light flux.

BRIEF DESCRIPTION OF THE DRAWINGS

The invention will be better understood by reading the following description, provided solely as an example, with references to the attached drawings in which.

Figure 1:
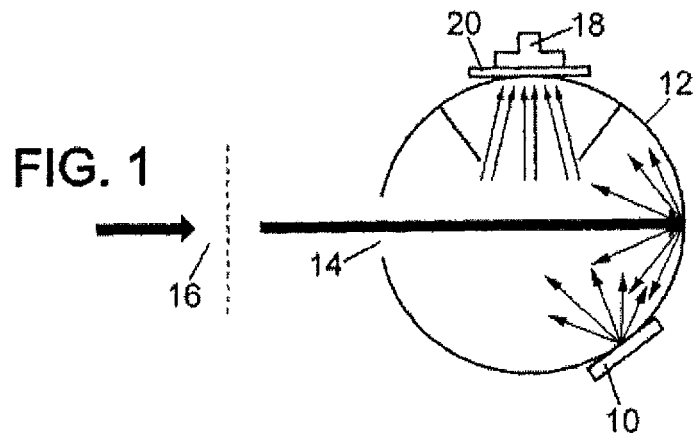
FIG. 1 is a schematic representation of a device which measures absorptivity of a photoconverter material according to an embodiment of the invention.

For clarity, the various elements represented in the figures are not necessarily to scale.

DETAILED DESCRIPTION OF THE DISCLOSURE

"Equivalent photoluminescence emission and absorption processes" in the invention is understood to mean processes of absorption and emission which geometrically correspond in a time-reversed manner. In one embodiment, the photoconverter material is illuminated such that the mean angle and the angular spread of the incident and emitted rays are the same.

In one embodiment of the invention, the photoconverter material is illuminated such that the light source and the photoconverter material are arranged so the angular distributions of the rays incident on and emitted by the illuminated surface of the material and collected by the detector are substantially the same.

The inventors have observed that under open circuit conditions, the energy emitted by luminescence by a photoconverter material can be related to a measurement of the capacity of the material to avoid losses due to electron recombination.

These losses due to electron recombination losses compete with the collectable electrical power, which means that the absolute luminescent flux emitted by a photoconverter material can be used to determine the maximum open circuit voltage (Vco) achievable in a complete device under the same illumination conditions.

The value of the open circuit voltage Vco of a photoconverter material can appear in the relation between the spectral radiation and the separation of quasi Fermi levels of the carriers qV. The inventors have observed that for a photoconverter material under certain conditions, the link between the spectral radiation and the separation of quasi Fermi levels of the carriers qV can be given by the generalized Planck equation:

$$I_{PL} = a(v2)\frac{2n_{v2}^2}{c^2}\frac{v^2}{\exp\left(\frac{hv - qVco}{kT}\right) - 1},$$

where
$I_{PL}$ is the photoluminescence intensity of the material,
$a(v2)$ is the absorptivity of the photoconverter measured at the second wavelength ($\lambda 2 = c*v2$) substantially equal to the photoluminescence wavelength of the photoconverter material and at the second light intensity I2,
$n_{v2}$ is the optical index of the photoconverter material at the photoluminescence wavelength of the photoconverter material,
c is the speed of the electromagnetic radiation in a vacuum,
v is the frequency corresponding to the photoluminescence wavelength of the photoconverter material,
h is the Planck constant,
k is the Boltzmann constant,
T is the surface temperature of the photoconverter,
q is the value of an elementary charge, and
Vco is the open circuit voltage of the photoconverter material.

The quantity q\*Vco represents the maximum free energy that can be extracted from the photoconverter material. It can be determined if the absorption and refractive indices, which allow determining the absorptivity a(v) at frequency v, are known.

The quantity q*Vco can be measured with an appropriate optical device, such as an integrating sphere for example, using Kirchoff's law by which the optical absorptivity and emissivity are equal at each frequency.

In one embodiment of the invention, the method of the invention comprises a first step of measuring the photoluminescence intensity of the photoconverter material.

As represented in FIG. 1, the photoconverter material 10 can be placed on one of the openings of an integrating sphere 12. The photoconverter material 10 is illuminated by a first light source, not represented. The first light source is placed outside the integrating sphere 12 and illuminates the photoconverter material 10 through an opening 14 in the integrating sphere 12.

The first light source illuminates the photoconverter material 10 at a first intensity I1 and at a first wavelength $\lambda 1$ corresponding to a first excitation energy greater than the absorption energy (Eg) of the photoconverter material 10.

In one embodiment, a device 16 which allows selecting the first wavelength $\lambda 1$ can be placed between the first light source and the photoconverter material 10. The photoconverter material 10 is placed in the integrating sphere 12 such that it is illuminated indirectly by the first light source. The processes of absorption of the incident radiation and photoluminescence are therefore equivalent, meaning that they geometrically correspond in a time-reversed manner, or that the angular distributions of the rays incident on and emitted by the illuminated surface of the material and collected by the detector are substantially the same.

In the embodiment represented in FIG. 1, the photoconverter material is illuminated such that the mean angle of incidence and the angular spread of the incident and photoluminescence rays are the same.

The photoluminescence intensity of the photoconverter material 10 can be measured by a measurement device 18 placed on an edge of the integrating sphere 12. Any measurement device known to a person skilled in the art may be used. In particular, a device may be used comprising a diode enabling light intensity measurement and a selective filter, for example a notch filter or a diffraction grating, to filter the wavelengths in order to measure the intensity only around the photoluminescence wavelength of the photoconverter material 10. Advantageously, the measurement device can be a spectrometer.

The method of the invention also comprises a step of measuring the absorptivity of the photoconverter material 10 at one of the detectable photoluminescence emission wavelengths of said photoconverter material 10.

Figure 2:
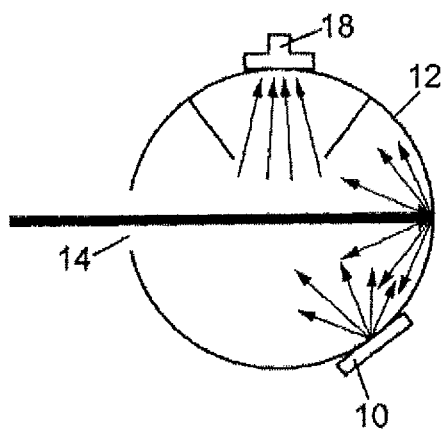
FIG. 2 is a schematic representation of a device which measures the photoluminescence intensity of a photoconverter material according to an embodiment of the invention.

In an embodiment of the invention as represented in FIG. 2, in order to measure the absorptivity, the photoconverter material 10 can be placed in an integrating sphere, for example the same one used for measuring the photoluminescence intensity.

The photoconverter material 10 is illuminated by a second light source at the second wavelength $\lambda 2$ and at a second light intensity I2 which is arbitrary but must be adapted to the sensitivity of the detector used.

Preferably, the second wavelength $\lambda 2$ is substantially equal to the photoluminescence wavelength of the photoconverter material, and the second light intensity I2 is substantially equal to the first intensity I1.

The photoconverter material 10 is arranged in the integrating sphere 12 in the same manner as for the photoluminescence measurement. Thus, the processes of incident radiation absorption and luminescence are equivalent, meaning that they geometrically correspond in a time-reversed manner, or that the angular distributions of the rays incident on and emitted by the illuminated surface of the material and collected by the detector are substantially the same.

Figure 3:
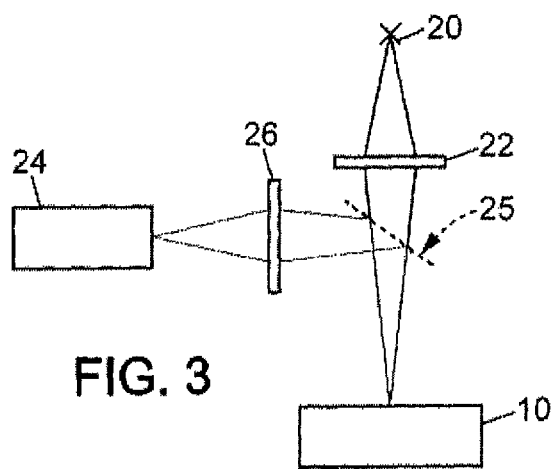
FIG. 3 represents a device which implements a method of the invention.

In the embodiment in FIGS. 2 and 3, the solid angle of the rays incident on and emitted by the illuminated surface of the material and collected by the detector is $2\pi$. The absorptivity of the photoconverter material 10 is obtained by measuring the reflectivity, assuming that the transmission of the photoconverter material 10 is practically zero. In one embodiment of the invention, a reflective surface can be placed behind the photoconverter material 10 in a manner that returns all incident light.

The generalized Planck equation is applicable in the measurement conditions represented in FIGS. 1 and 2. It allows deducing the maximum open circuit voltage Vco of the photoconverter material 10 for the absorptivity and photoluminescence measurements.

In one embodiment of the invention, it is also possible to measure the photoluminescence intensity and the absorptivity of the photoconverter material 10, using an optical assembly which allows the solid angle of illumination of the photoconverter material 10 to be substantially equal to the solid angle of collection of the optical measurement device.

One example of such an optical assembly is represented in FIG. 3.

The photoconverter material 10 is illuminated by a light source 20. The radiation issuing from the light source 20 is focused on the photoconverter material by using a first optical device 22, comprising, for example, a convergent lens.

The optical assembly is configured such that the axis of the incident light radiation is substantially perpendicular to the plane of the photoconverter material 10.

The incident radiation is divided preferably by means of a partially reflective plate placed between the first optical device 22 and the photoconverter material 10 in a manner that forms an angle of approximately 45° with the axis of the incident light radiation.

The radiation reflected or emitted by photoluminescence by the photoconverter material 10 is directed towards a measurement device 24 via the semi-reflective plate 25 and a second focusing device 26. The second focusing device can comprise a convergent lens, focusing on the measurement device 24 the radiation reflected or emitted by photoluminescence.

In one embodiment of the invention, the photoconverter material 10 can be illuminated with a reference solar spectrum, the spectral portion near and below the absorption threshold Eg of the photoconverter material being filtered so that the photoluminescence can be detected near the absorption threshold Eg. In this case, the photoluminescence intensity in the emission band close to the absorption threshold Eg enables to estimate the free energy extractible from the material under this same illumination.

Under given excitation conditions, the absorptivity measurement for the photoconverter material 10 in a spectral range greater than the absorption threshold of the material and covering the spectrum to be converted enables to provide the maximum photocurrent which can be generated under these same illumination conditions. In fact, the photocurrent is limited by the amount of photons absorbed, in the usual cases where an absorbed photon can only produce a single electron/hole pair.

The number and choice of points in the spectral range determine the precision of the value determined for the open circuit voltage.

In photovoltaic structures that are optimized and/or good materials, the collection of photogenerated carriers is good and the internal quantum yield is in fact close to the absorptivity of the photoconverter material, for example between 80 and 90%. Measurements of conductivity, or even of mobility, according to known methods can support the hypothesis of effective collection.

The invention also relates to a method of determining the energy efficiency of a photoconverter material exposed to a measurement light intensity I0.

The method for determining the efficiency may additionally comprise a step of determining the maximum open circuit voltage (Vco) of the photoconverter material at a measurement light intensity I0 using a method of the invention.

The method of determining the efficiency according to the invention additionally comprises a step of determining the photocurrent of the photoconverter material. The photocurrent can be determined by measuring the absorptivity of the material at different wavelengths in order to cover the spectrum to be converted. The number of values determined governs the precision of the determination made.

In one embodiment of the invention, the photocurrent of the photoconverter material is determined by means of the following equation:

$$Icc = \int a(v)\Phi(v)dv$$

where
Icc is the determined photocurrent of the photoconverter material,
$a(v)$ is the absorptivity of the photoconverter material at the measurement light intensity I0, and
$\Phi(\mu)$ is the incident light flux.

The inventors have observed that the incident light flux affects both the photocurrent as well as the maximum open circuit voltage Vco. Plotting the photocurrent Icc as a function of the maximum open circuit voltage Vco for a range of incident fluxes yields the voltage-current characteristic of the photoconverter material.

Based on the voltage-current characteristic of the photoconverter material, a person skilled in the art can deduce the dark current, meaning the residual electric current in the photoconverter material in the absence of illumination. The dark current allows obtaining the amount of radiative recombination in order to find the radiative efficiency.

The energy efficiency of the photoconverter material at light intensity I0 is proportional to the product of the maximum open circuit voltage Vco and the photocurrent.

The invention is not limited to the embodiments described and is not to be interpreted in a limiting manner. It encompasses any equivalent embodiment. In particular, the generalized Planck equation is applicable to any system having several absorption thresholds, or multiphoton absorptions, meaning processes with multiple photons.

The invention claimed is:

1. A method for determining the maximum open circuit voltage of a photoconverter material exposed to a measurement light intensity, said method comprising the following steps:
the photoluminescence intensity of the photoconverter material is measured by illuminating the photoconverter material using a first light source at a first light intensity and at a first wavelength corresponding to a first excitation energy greater than the absorption energy of the photoconverter material, the first light intensity being substantially equal to the measurement light intensity;
the absorptivity of the photoconverter material is measured at a second wavelength substantially equal to one of the photoluminescence wavelengths of the photoconverter material, by illuminating the photoconverter material using a second light source at the second wavelength and at a second light intensity; and
the maximum open circuit voltage of the photoconverter material at the measurement light intensity is determined using the absorptivity and the photoluminescence intensity, both measured at substantially the same wavelength,
wherein the light source and the photoconverter material are arranged such that the angular distributions of the rays incident on and emitted by the illuminated surface of the material and collected by the detector are substantially the same.

2. The method according to claim 1, wherein the open circuit voltage is determined using the following equation:

$$I_{PL} = a(v2)\frac{2n_{v2}^2}{c^2}\frac{v^2}{\exp\left(\frac{hv - qVco}{kT}\right) - 1},$$

where
IPL is the photoluminescence intensity of the photoconverter material, measured by illuminating the photoconverter material at the first light intensity;
$a(v2)$ is the absorptivity of the photoconverter, measured at the second wavelength ($\lambda 2 = c*v2$) substantially equal to the photoluminescence wavelength of the photoconverter material and at the second light intensity;
is the optical index for the photoconverter material at the photoluminescence wavelength of the photoconverter material;
c is the speed of the electromagnetic radiation in a vacuum;
v is the frequency corresponding to the photoluminescence wavelength of the photoconverter material;
h is the Planck constant;
k is the Boltzmann constant;
T is the surface temperature of the photoconverter;
q represents the value of an elementary charge; and
Vco is the open circuit voltage of the photoconverter material.

3. The method according claim 1, wherein the photoconverter material, the first and second light sources, and the optical measurement device are arranged such that the solid angle of illumination of the photoconverter material is substantially equal to the solid angle of collection of the optical measurement device.

4. The method according to claim 1, wherein the photoconverter material is placed in an integrating sphere structure such that it is indirectly illuminated by the first and second light sources.

5. The method according to claim 1, wherein the measurements of photoluminescence intensity and/or absorptivity are made using a diode or spectrometer.

6. A method for determining the energy efficiency of a photoconverter material, said method comprising the following steps:
the maximum open circuit voltage of the photoconverter material is determined at a measurement light intensity by a method according to claim 1;
the photocurrent of the photoconverter material is determined by measuring the absorptivity of the material at a third light intensity substantially equal to the measurement light intensity and at different wavelengths;
the energy efficiency of the photoconverter material is determined at the light intensity according to:

Efficiency=$Vco*Icc*FF/Pinc$, where
- Icc is the photocurrent of the photoconverter material;
- Vco is the maximum open circuit voltage of the photoconverter material;
- FF is the form factor of the photoconverter material; and
- Pinc is the incident power.

7. The method according to claim 6, wherein the photocurrent of the photoconverter material is determined using the following equation:

$$Icc = \int a(\nu)\Phi(\nu)d\nu,$$

where
- Icc is the determined photocurrent of the photoconverter material;
- $a(\square)$ is the absorptivity of the photoconverter material at the measurement light intensity I0; and
- $\Phi(\square)$ is the incident light flux.

8. A method for determining the power extractible from a photoconverter material illuminated by a light source of intensity, said method comprising the following steps:
- the maximum open circuit voltage Vco of the photoconverter material is determined, at a plurality of light intensities, by a method comprising the following steps:
  - the photoluminescence intensity of the photoconverter material is measured by illuminating the photoconverter material using a first light source at a first light intensity and at a first wavelength corresponding to a first excitation energy greater than the absorption energy of the photoconverter material, the first light intensity being substantially equal to the measurement light intensity;
- the absorptivity of the photoconverter material is measured at a second wavelength substantially equal to one of the photoluminescence wavelengths of the photoconverter material, by illuminating the photoconverter material using a second light source at the second wavelength and at a second light intensity; and
- the maximum open circuit voltage of the photoconverter material at the measurement light intensity is determined using the absorptivity and the photoluminescence intensity, both measured at substantially the same wavelength, wherein the light source and the photoconverter material are arranged such that the angular distributions of the rays incident on and emitted by the illuminated surface of the material and collected by the detector are substantially the same; and the photocurrent Icc of the photoconverter material is determined by a method according to claim 6; and the power extractible from the photoconverter material is determined by plotting Icc as a function of Vco.

\* \* \* \* \*